United States Patent
Verri Lima

(10) Patent No.: US 9,713,328 B2
(45) Date of Patent: Jul. 25, 2017

(54) HYPERBARIC CRIOGENESIS CHAMBERS

(76) Inventor: Gaston Jeronimo Verri Lima, Montevideo (UY)

(*) Notice: Subject to any disclaimer, the term of this patent is extended or adjusted under 35 U.S.C. 154(b) by 1355 days.

(21) Appl. No.: 11/913,448

(22) PCT Filed: May 2, 2006

(86) PCT No.: PCT/IB2006/001146
§ 371 (c)(1),
(2), (4) Date: Nov. 2, 2007

(87) PCT Pub. No.: WO2006/117658
PCT Pub. Date: Nov. 9, 2006

(65) Prior Publication Data
US 2008/0213825 A1    Sep. 4, 2008

(30) Foreign Application Priority Data
May 2, 2005    (UY) .......................................... 28881

(51) Int. Cl.
*A01N 1/02*    (2006.01)
(52) U.S. Cl.
CPC ......... *A01N 1/0289* (2013.01); *A01N 1/0257* (2013.01); *A01N 1/0284* (2013.01)
(58) Field of Classification Search
None
See application file for complete search history.

(56) References Cited

U.S. PATENT DOCUMENTS

| | | | |
|---|---|---|---|
| 3,257,820 A * | 6/1966 | Case et al. ....................... | 62/223 |
| 5,084,011 A * | 1/1992 | Grady .............................. | 604/24 |
| 5,899,846 A | 5/1999 | Sternberg et al. | |
| 5,935,516 A | 8/1999 | Baugh | |
| 6,120,985 A | 9/2000 | Laugharn, Jr. et al. | |
| 6,269,649 B1 * | 8/2001 | Studer ............................ | 62/51.1 |
| 6,748,760 B1 | 6/2004 | Cheng et al. | |
| 2003/0232114 A1 | 12/2003 | Dekleva | |

FOREIGN PATENT DOCUMENTS

| | | |
|---|---|---|
| DE | 19922310 | 11/2000 |
| JP | 2004242581 | 9/2004 |
| SU | 567450 | 8/1977 |

OTHER PUBLICATIONS

Statebourne Cryogenics "Helistor Series" <http://www.statebourne.com/helium_dewars.html#open>, 2002, 1 page.*
Waisman, D; Shupak, A; Weisz, G; and Melamed, Y "Hyperbaric Oxygen Therapy in the Pediatric Patient: The Experience of the Israel Naval Medical Institute" Pediatrics 1998,102(5),e53, 11 pages.*
Dahl, Rolf and Staehelin, L. Andrew "High-pressure Freezing for the Preservation of Biological Structure: Theory and Practice" Journal of Electron Microscopy Technique, 1989, 13(3), pp. 165-174.*
D'Aoust, Brian G. "Apparatus for Incubating and Sampling Tissue and/or Cell-Free Systems Under Elevated Gas Pressure" Anal. Biochem. 1968, 26, pp. 85-91.*
USFDA "Hyperbaric Oxygen Therapy: Don't Be Misled" FDA Consumer Health Information, Aug. 2013, 2 pages.*
Moor, Hans, "Chapter 8: Theory and Practice of High Pressure Freezing" , in Cryotechniques in Biological Electron Microscopy, Springer-Verlag, Berlin, 1987, pp. 175-191.*
Studer, D et al "Vitrification of articular cartilage by high-pressure freezing" J Microscopy, 1995, 179(3), 321-332.*
Shecterle, LM; Kelly, T; and St Cyr, JA "Safe and efficient extracorporeal method of inducing whole body hyperthermia", International Journal of Hyperthermia, 12(4), pp. 569-571, DOI: 10.3109/02656739609023532.*
FDA "Hyperbaric Oxygen Therapy: Don't Be Misled" USFDA Consumer Health Information, UCM366015, Aug. 2013, pp. 1-2.*
Jansen, HJ "Titanium in a Hyperbaric Oxygen Environment May Pose a Fire Risk" Aviation, Space, and Environmental Medicine, Dec. 2003, 74(12), pp. 1301-1302.*
Shecterle, LM; Kelly, T; and St Cyr, JA "Safe and efficient extracorporeal method of inducing whole body hyperthermia", International Journal of Hyperthermia, 1996, 12(4), pp. 569-571, DOI: 10.3109/02656739609023532.*
Database WPI Week 197824; Derwent Publications Ltd., London, GB; AN; 1978-E7096A; XP002400360 & SU 567 450 A (Olkhovoj), Sep. 23, 1977, abstract.
St. Peter et al., "Liver and kidney preservation by perfusion", Lancet The, Lancet Limited, London, GB, Feb. 16, 2002, 604-613, vol. 359(9306).
International Search Report issued Oct. 6, 2006 during the prosecution of International Patent Application No. PCT/IB2006/001146, 5 pages.

* cited by examiner

*Primary Examiner* — Chris R Tate
*Assistant Examiner* — Aaron J Kosar
(74) *Attorney, Agent, or Firm* — Inventions International Inc.; Tiffany C. Miller

(57) ABSTRACT

The Hyperbaric Cryogenesis Chambers are equipment for medical usage, extracorporeal, and capable of promoting the proliferation and preservation of cells in a way mainly microbiologic, "not biologic". They are compartments with containers that host tissues or cells in solution with nutrients, that bear pressures higher and lower to sea level. They have a cold system inside that lowers the environmental temperature and maintains it permanently. They are for maintaining viability of cells or tissues and to induce their organized proliferation with oxygen or other gases at pressures higher or lower that the exterior of the chamber.

2 Claims, 1 Drawing Sheet

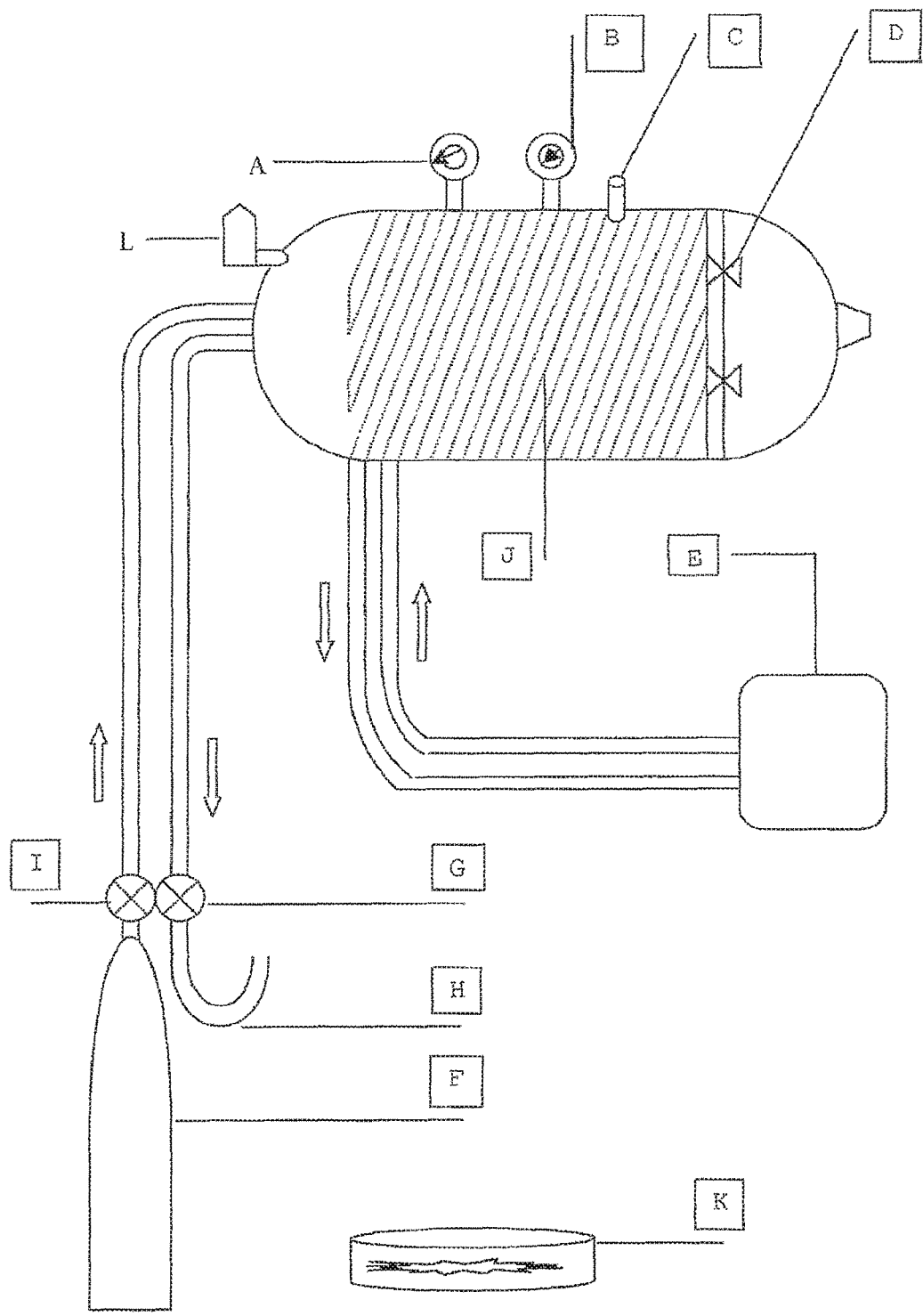

HYPERBARIC CRIOGENESIS CHAMBERS

BACKGROUND OF THE INVENTION

1. Field of the Invention

This invention relates, generally, to a hyperbaric cryogenesis chamber. More particularly, it relates to a hyperbaric cryogenesis chamber having a compartment with the capacity to be pressurized to pressures superior to the equivalent of an atmosphere of pressure (760 mmHg) and depressurized in an intermittent way, with whatever mixture of gases such as pure oxygen, compressed air, Nitrox, Heltiox, Trimix, and/or anesthetic gases. Inside the hyperbaric cryogenesis chamber, there is a system which contains liquid or semi-liquid elements such as, cells, complete or incomplete organic tissues, complete organs or fractions of them, and/or human bodies or dead animals. The hyperbaric cryogenesis chamber can have in internal or external hermetic system in order to lower the environment temperature. The hyperbaric cryogenesis chamber may have an illumination system such as, optic and microscopic visualization, optic or chamber fibroscopy, or environment temperature sensors. The hyperbaric cryogenesis chamber has pressure manometers and over-pressure safety valves. The sizes of the hyperbaric cryogenesis chamber are variable.

2. Background Art

There are no known solutions regarding the combination of induction of the cellular proliferation in an extracorporeal manner and in an organized way. Thus, there is a need for an extracorporeal induction of the proliferation in one or a few cellular types while maintaining cellular integrity and while provoking the descent of the temperature in compartments which hold them with physiological fluids under intermittent pressure with pure oxygen. There are no known solutions which combine both events in order to induce nonproliferation and/or lysis of tumoral cells by direct action of free radicals of oxygen under conditions of raised pressure and of cold temperature. Prior art hyperbaric chambers have been used for more than one hundred years to help patients with including, but not limited to, decompression or diving accidents, skin wounds, infections, burns, fractures, compartment syndromes, refractory mycosis, intoxication, and other diseases. For example, the patient is helped by introducing the patient to the hyperbaric chamber. When the hyperbaric chamber is pressurized inside and reaches values higher than an atmosphere, pure oxygen is administered for the patient to breathe. This results in microbiologic effects. The pressurization is realized with the compressed air in the multi-seater chambers or pure oxygen in single-seaters. Pure oxygen is breathed in by the patient under higher pressure than found at sea level by utilizing the closed circuit systems in the multi-seater chambers. The Hyperbaric Chambers were classified in three categories as follow: 1) Type A, for human beings and multi-seater. 2) Type B, for human beings and single seater. 3) Type C, for experimentation and animals.

The cryo-preservation of tumoral cells and to induce nonproliferation or the lysis of tumoral cells is a technique used by hemotherapists in the field of hemato-oncology. However, this preservation is not permanent. Hyperbaric oxygenation has been used in order to accelerate the wound cicatrisation of patients. For example, this may be done by introducing a patient to a hyperbaric chamber and having the patient inhale pure oxygen intermittently while being under an environment pressure higher than sea level (one atmosphere or 760 mmHG) for a period that may reach an hour and twenty minutes. In this example, the speed of cellular reproduction is accelerated in the affected area in an organized way. However, the proliferation of cells of determined types are not realized in an extracorporeal manner. Further, it is also of public knowledge that the handling of samples of tissues or cells in cold conditions preserves the cells. This is seen in animal insemination for more than three decades.

BRIEF SUMMARY OF THE INVENTION

The advantages in the use of the hyperbaric cryogenesis chamber is establishing a combination of both techniques in order to induce reproduction of cells of a cellular type Cells of a cellular type being mixed with tumoral cells can be processed with viability being maintained for a longer period of time. Additionally, at the same time it fosters the lysis or the nonproliferation of tumoral cells at a higher speed than these techniques allow separately and furthermore in an extracorporeal manner. This combination of cryopreservation and hyperbaric oxygen therapy with the processing in a hyperbaric cryogenesis chamber accelerates cellular reproduction of various types. This technique may be helpful in pathologies such as leukemia in its terminal phase and hepatopathology with cirrhosis in its terminal stage for determining the possibility of using an implant when the number of these cells is already insufficient. Thus, the industrial exploitation is realized in areas including, but not limited to, hospitals. For example, a hospital can utilize this technique of using the hyperbaric cryogenesis chamber in order to process cells or tissues for the treatment of diseases in an extracorporeal manner. This invention with the adequate technique allows the preservation of human corpses or dead animals for longer periods of time.

In order to build a hyperbaric cryogenesis chamber, it is necessary to build chambers capable of being pressurized to pressures up to 10 kg per square centimeter with certified steel or an aluminum plate (pursuant to ISO standards on Hyperbaric Chamber types A, B, or C). A refrigerating system can be located inside or outside of the hyperbaric cryogenesis chamber. The refrigerating system is characterized by hermetic steel or aluminum tubing able to bear pressure and permit the installation of another tubing, made preferably of copper, within the tubing. The tubing that is preferably made of copper is the tubing which allows the circulation of refrigerating gas in its inside, isolated from the steel or aluminum by a compacted cotton net. The copper tubing is connected to a motor for the circulation of gas under electric propulsion. The hyperbaric cryogenesis chamber can hold receptacles preferably made of glass. These named containers have the capacity to store physiologic fluids, cells, tissues, organs, human bodies, or dead animals.

The hyperbaric cryogenesis chamber may be transportable or fixed.

BRIEF DESCRIPTION OF THE DRAWINGS

For a fuller understanding of the nature and objects of the invention, reference should be made to the following detailed description, taken in connection with the accompanying drawing, in which:

FIG. 1 is a top plan view of the novel hyperbaric cryogenesis chamber connected to a hermetic cooling system and connected to a supply system of gasses. In FIG. 1, A illustrates a manometer which registers the pressure of the internal environment of the hyperbaric cryogenesis chamber J.

FIG. 1 shows thermometer B which registers the temperature of the internal environment of the hyperbaric cryogenesis chamber J.

As depicted in FIG. 1, observation system C can have glass resistant to 10 kg/cm$^2$ of pressure or fibroscopy for internal observation with microscopy or a camera connected to a monitor.

FIG. 1 illustrates standard cranks D of the door of the hyperbaric cryogenesis chamber J to facilitate the opening and the closing of the door.

FIG. 1 shows cold generator E with a closed circuit and an inner chamber system that is isolated with no static material.

As shown in FIG. 1, supply system of gases F has a higher pressure interchangeable with pure oxygen or of an exclusive supply of pure oxygen under pressure.

FIG. 1 illustrates decompression valves G.

FIG. 1 illustrates exhaust system or decompression system H.

FIG. 1 illustrates compression system I with its corresponding valves.

FIG. 1. Illustrates hyperbaric cryogenesis chamber J connected with a closed circuit of the refrigerating system E and circulating system of gases F under pressure.

FIG. 1 illustrates container K. Container K can retain physiologic fluids, cells, tissues, organs, and bodies. Container K can retain essential nutrients or not retain its essential nutrients. Container K is made with or without micrometric gradation located at the bottom of the container. It is within the scope of the current invention for container K to be made preferably of glass.

FIG. 1 illustrates overpressure safety valve L.

DETAILED DESCRIPTION OF THE PREFERRED EMBODIMENT

The hyperbaric cryogenesis chambers allow storage and processing of tissues or organs for the induction of the proliferation of the cellular type in an organized way. For example, the tumoral cells will not proliferate. The hyperbaric cryogenesis chambers also permit the induction in the nonproliferation or the lysis of eventual tumoral cells. Tumoral cells will be defined as disorganized of those partial or complete samples of tissues or organs in accordance with its processing. To achieve this, samples of cells having a nucleus must be kept isolated. The cells can include mother cells, epithelial, pancreatic, neurons, fibroblasts, hepatic cells, muscular cells, ovocytes, or spermatozoids. The samples of cells having a nucleus are retained in receptacles (named containers). It is within the scope of this invention for the cells to be partial tissue, total tissue, a partial organ, or a complete organ. The temperature decreases from values close to 37 degrees Celsius to approximately −70 degrees Celsius with the same environment pressure to that of sea level (that is to say without modifying the pressure). For instance, the isolated cells having a nucleus are retained in receptacles. The receptacles are containers of various sizes according to necessities. The isolated cells with the particularity that remain from the beginning of the process can be in a solution with physiologic fluids such as serum, plasma, plasmatic substitutes. The solution with physiologic fluids is in association with essential nutrients. Essential nutrients include preparations of parenteral nutrition or anything similar. The essential nutrients may be with or without vitamins and/or minerals. Further, the isolated cells in solution are under physiological conditions of pH and are being preserved by the descent in temperature to variable values depending on the cellular type that may surpass −70 degrees Celsius. Afterwards, depending upon the cellular type to be processed a programmed rise in temperature occurs inside the hyperbaric cryogenesis chamber. The environment pressurization reaches values higher than an atmosphere of pressure and could reach pressures up to 7 atmospheres. The compression or pressurization is realized with gases such as, pure oxygen, compressed air, or gas mixtures. It is within the scope of this current invention for gas mixtures to include, anesthetic gases, nitric oxide, Trimix, Heliox, Nitrox, etc., to be substituted by pure oxygen one hundred percent. The time of pressurization can vary and can be more than an hour with a sequence during the day. The time of pressurization is also variable in that it may be once or as many times as necessary in order to obtain the cellular sample according to its requirement. Once obtained, the time of pressurization is pre-established to process the sample. The next step is decompression and lowering of the temperature inside the hyperbaric cryogenesis chamber so as to reach the initial values.

The hyperbaric cryogenesis chambers allow with this procedure the induction in the nonproliferation or the lysis of disorganized cells (tumorals) of a sample. This is accomplished by the direct action of cold and the direct action of free radicals of oxygen obtained in conditions of saturation at pressures higher than an atmosphere with a gas. The viability disturbance and proliferation of tumoral or disorganized cells is by exposition to cold and free radicals.

In this procedure, the hyperbaric cryogenesis chambers may be operated manually or by programmed control with computers.

These hyperbaric cryogenesis chambers can have an optic or microscopic visualization system, or by way of chambers of the samples through optic fibroscopy.

STATE OF THE ART

It is a novelty, the creation of hyperbaric cryogenesis chambers taking advantage of the incorporation of both techniques for the microbiologic processing activity. Processing that in its procedure leads to preservation and induction of organized proliferation of isolated cell samples or as tissues or organs in forms of partial or complete. The processing activity being under sequence variations of temperature and pressure with pure oxygen and nutrients in dissolution in a medium of physiologic fluids which hosts the cells. Also, with the hyperbaric cryogenesis chambers, we get the induction in the nonproliferation of disorganized or tumoral cells or the lysis of them by the associated action of free radicals and the cold temperature.

I claim as my property:

1. A hyperbaric cryogenesis chamber system for use in extracorporeal induction of the proliferation of at least one cell, comprising:

a hyperbaric cryogenesis chamber having at least one compartment, said at least one compartment of said hyperbaric cryogenesis chamber is configured to be pressurized to pressures up to 10 kg per square centimeter, said at least one compartment of said hyperbaric cryogenesis chamber is configured to be depressurized intermittently;

a solution having at least one physiological fluid, a plurality of nutrients, and said at least one cell;

at least one receptacle, whereby, said at least one receptacle retaining said solution, whereby, said at least one compartment of said hyperbaric cryogenesis chamber is configured to retain said at least one receptacle;

a hermetic cooling system having a refrigeration unit, said refrigeration unit is connected to an end of an insulated tubing, said insulated tubing having a first tubing and a second tubing, said second tubing is located inside of said first tubing, said second tubing is isolated from said first tubing by an insulating material, a portion of said second tubing is in thermal communication with said hyperbaric cryogenesis chamber, a force generated from the propulsion of a motor is configured to circulate a refrigerant within said second tubing from said refrigerating unit to said portion of said second tubing in thermal communication with said hyperbaric cryogenesis chamber, said refrigerant absorbs heat within said hyperbaric cryogenesis chamber, thereby, cooling said hyperbaric cryogenesis chamber, and then returning said refrigerant back to said refrigerating unit, said hermetic cooling system is configured to lower a temperature value inside of said at least one compartment of said hyperbaric cryogenesis chamber to approximately −70° C.; and, a vessel, said vessel is connected to said hyperbaric cryogenesis chamber, said vessel retaining at least one compressed gas, wherein said at least one compressed gas is or comprises oxygen.

2. A hyperbaric cryogenesis chamber system for use in extracorporeal induction of the lysis of at least one disorganized cell, comprising:

a hyperbaric cryogenesis chamber having at least one compartment, said at least one compartment of said hyperbaric cryogenesis chamber is configured to be pressurized to pressures up to 10 kg per square centimeter, said at least one compartment of said hyperbaric cryogenesis chamber is configured to be depressurized intermittently;

a solution having at least one physiological fluid, a plurality of nutrients, and said at least one disorganized cell;

at least one receptacle, whereby, said at least one receptacle retaining said solution, whereby, said at least one compartment of said hyperbaric cryogenesis chamber is configured to retain said at least one receptacle;

a hermetic cooling system having a refrigeration unit, said refrigeration unit is connected to an end of an insulated tubing, said insulated tubing having a first tubing and a second tubing, said second tubing is located inside of said first tubing, said second tubing is isolated from said first tubing by an insulating material, a portion of said second tubing is in thermal communication with said hyperbaric cryogenesis chamber, a force generated from the propulsion of a motor is configured to circulate a refrigerant within said second tubing from said refrigerating unit to said portion of said second tubing in thermal communication with said hyperbaric cryogenesis chamber, said refrigerant absorbs heat within said hyperbaric cryogenesis chamber, thereby, cooling said hyperbaric cryogenesis chamber, and then returning said refrigerant back to said refrigerating unit, said hermetic cooling system is configured to lower a temperature value inside of said at least one compartment of said hyperbaric cryogenesis chamber to approximately −70° C.; and, a vessel, said vessel is connected to said hyperbaric cryogenesis chamber, said vessel retaining at least one compressed gas, wherein said at least one compressed gas is or comprises oxygen.

\* \* \* \* \*